United States Patent
Hanson et al.

(10) Patent No.: US 12,102,611 B2
(45) Date of Patent: Oct. 1, 2024

(54) COMPOSITIONS AND METHODS FOR TREATING HYPERTENSION BY MODULATING ENDOCRINE ACTIVITY

(71) Applicant: Olfactive Biosolutions, LLC, Mountain View, CA (US)

(72) Inventors: Christopher Hanson, Mountain View, CA (US); William Harries, Colden, NY (US)

(73) Assignee: Olfactive Biosolutions, LLC, Mountain View, CA (US)

( * ) Notice: Subject to any disclaimer, the term of this patent is extended or adjusted under 35 U.S.C. 154(b) by 0 days.

(21) Appl. No.: 18/615,452

(22) Filed: Mar. 25, 2024

(65) Prior Publication Data
US 2024/0269100 A1    Aug. 15, 2024

(51) Int. Cl.
*A61K 31/22*    (2006.01)
*A61K 31/19*    (2006.01)
*A61P 9/12*    (2006.01)

(52) U.S. Cl.
CPC ............ *A61K 31/22* (2013.01); *A61K 31/19* (2013.01); *A61P 9/12* (2018.01)

(58) Field of Classification Search
CPC ............ A61K 31/19; A61K 31/22; A61P 9/12
See application file for complete search history.

(56) References Cited

FOREIGN PATENT DOCUMENTS

WO    WO-2017042337 A1 *    3/2017    ............ A61K 31/19

OTHER PUBLICATIONS

Xu, et al. "Short-chain fatty acid receptors and blood pressure regulation . . . " Hypertension 79, No. 10 (2022), pp. 2127-2137.
Pluznick, JL. "Microbial short-chain fatty acids and blood pressure regulation." Current hypertension reports 19 (2017), pp. 1-5.

* cited by examiner

*Primary Examiner* — Kevin E Weddington
(74) *Attorney, Agent, or Firm* — Francis Law Group (57) ABSTRACT

Disclosed herein are compounds and ligands, and antihypertensive compositions formed therewith, that modulate seminal endocrine factors that control blood pressure and, thereby, treat hypertension. Also disclosed herein are methods for using the antihypertensive compositions to treat hypertension and disorders associated therewith.

5 Claims, 1 Drawing Sheet

COMPOSITIONS AND METHODS FOR TREATING HYPERTENSION BY MODULATING ENDOCRINE ACTIVITY

FIELD OF THE INVENTION

The present invention relates to compositions and methods for treating hypertension. More particularly, the present invention relates to compositions and methods for treating hypertension by modulating G-protein coupled receptor activity.

BACKGROUND OF THE INVENTION

Hypertension is one of the most widespread chronic diseases in the U.S. and is estimated by the Centers for Disease Control and Prevention (CDC) to cost the United States over $131 billion a year in healthcare costs. The CDC also estimates that at least 47% of U.S. adults (i.e., approximately 121.5 million adults) are afflicted with hypertension, where hypertension is defined as a systolic blood pressure greater than 130 mmHg, a diastolic blood pressure greater than 80 mmHg, or are prescribed medication for hypertension.

As is well established, hypertension significantly increases the risk of developing numerous life-threatening diseases and disorders, such as hypertensive heart disease, myocardial infarction (i.e., heart attack), heart failure, renal failure, aneurysm, and stroke, which are leading causes of death in the U.S. In 2021, hypertension was a primary or contributing cause of approximately 691,095 deaths in the United States.

As is also well established, one of the most common types of hypertension is essential (or primary) hypertension, which is a category of hypertension characterized by a systolic blood pressure greater than 130 mmHg or a diastolic blood pressure greater than 80 mmHg without a single, distinct underlying cause.

Recent studies have shown that essential hypertension is associated with dysregulation of the renin-angiotensin-aldosterone system (RAAS), which is a core blood pressure regulation system that regulates angiotensin II (Ang II) and aldosterone, two seminal blood pressure-increasing endocrine factors. The studies specifically found that dysregulation of the RAAS system results in elevated levels of Ang II and aldosterone, which activate NADPH oxidase in vascular walls to generate elevated concentrations of reactive oxygen species (ROS), such as $O_2^-$ and $H_2O_2$, to induce vasoconstriction and, thereby, increase blood pressure to hypertensive levels.

The studies have also established that the excess levels of ROS will also activate the mitogen-activated protein kinase (MAPK) cell signaling pathway associated with endogenous cell proliferation, and the Smad-dependent transforming growth factor beta (TGF-β) cell signaling pathway associated with collagen synthesis, which results in thickening and fibrosis of vascular walls and, thereby, vascular dysfunction and persistent hypertension.

Various entities have thus developed blood pressure reducing pharmaceutically active agents and therapies that treat essential hypertension. Such pharmaceutically active agents include angiotensin-converting enzyme (ACE) inhibitors, angiotensin II receptor blockers (ARBs), beta blockers, calcium channel blockers, diuretics, renin inhibitors, and vasodilators.

Although the noted pharmaceutically active agents and therapies have generally been deemed effective means for treating essential hypertension, there are several drawbacks and disadvantages associated with the above noted pharmaceutically active agents.

A major drawback and disadvantage associated with the noted pharmaceutically active agents is that there is a myriad of side effects associated with administration of the pharmaceutically active agents to a subject. By way of example, the side effects associated with the administration of ACE inhibitors include dry cough, tiredness, dizziness, headaches and loss of taste, and the side effects associated with the administration of beta blockers include cold hands/feet, tiredness, dizziness, weight gain, depression, shortness of breath, and difficulty sleeping.

A further drawback and disadvantage associated with the noted pharmaceutically active agents is that many subjects are often prescribed multiple types of pharmaceutically active agents to aggressively treat severe cases essential hypertension. Subjects taking multiple types of pharmaceutically active agents must often endure the adverse physiological effects associated with calibrating the minimum effective dosages of multiple agents and the side effects associated with the administration of multiple agents.

Further, some of the agents cannot be combined due to the risk of serious complications. By way of example, ACE inhibitors and ARBs cannot be administered to a subject with renin inhibitors due to severe stroke risk.

A further drawback and disadvantage associated with the noted pharmaceutically active agents is that, in some instances, subjects present with hypertension that is broadly resistant to the above noted pharmaceutically active agents, which is commonly referred to as resistant hypertension. Resistant hypertension often requires more aggressive treatment measures and can be very difficult to treat with pharmaceutically active agents alone.

Although surgical methods of treating hypertension, such as renal denervation, have also generally been deemed effective means for treating resistant hypertension, surgical methods are (i) invasive, (ii) require general anesthetization of a subject, and (iii) are generally only appropriate for treating resistant hypertension characterized by renal nerve hyperactivity.

There is thus a need for improved compositions and methods to treat hypertension, which substantially reduce or overcome the drawbacks and disadvantages associated with conventional blood pressure reducing pharmaceutically active agents and therapies.

There is also a need for improved compositions and methods to lower blood pressure in hypertensive subjects with minimal side effects.

It is thus one object of the present invention to provide improved compositions and methods for treating hypertension that overcome the drawbacks and disadvantages associated with administration of conventional blood pressure reducing pharmaceutically active agents to patients.

It is another object of the present invention to provide improved compositions that effectively modulate the endocrine system of a patient with minimal side effects, which can be administered to the patient via oral, sublingual, inhalation, intranasal, epidural, intracerebral, transdermal, topical, and injection administration means.

It is another object of the present invention to provide improved compositions that can effectuate receptor modulation of endogenous renin in a patient, which can be administered to the subject without the undesirable side effects associated with administration of conventional blood pressure reducing pharmaceutically active agents to patients.

It is another object of the present invention to provide improved compositions that can effectuate receptor modulation of vasodilation in a patient, which can be administered to the subject without the undesirable side effects associated with administration of conventional blood pressure reducing pharmaceutically active agents to patients.

It is another object of the present invention to provide improved compositions that can effectively treat adverse hypertensive endocrine responses and, hence, hypertensive endocrine diseases and disorders associated therewith without the undesirable side effects associated with administration of conventional blood pressure reducing pharmaceutically active agents to patients.

SUMMARY OF THE INVENTION

The present invention is directed to compositions and methods for treating hypertension and diseases and disorders associated therewith.

In some embodiments of the invention, there are thus provided compositions for treating hypertension and diseases and disorders associated therewith.

In one embodiment of the invention, the composition for treating hypertension and hypertension-associated diseases and disorders (referred to herein as "an antihypertensive composition" comprises a delivery medium, propionic acid and butyrate, the antihypertensive composition adapted to induce at least serotonin (5-HT), secretin, prostaglandin E2 and vasoactive intestinal protein secretion in vivo, whereby, when the antihypertensive composition is delivered to a patient, vasodilation is induced.

In a preferred embodiment, the antihypertensive composition is sufficient to induce at least 50% activation of olfactory receptor OR51E1, olfactory receptor OR51E2, free fatty acid receptor FFAR2, free fatty acid receptor FFAR3 and/or hydroxycarboxylic acid receptor GPR109A in vivo when the antihypertensive composition is delivered to a patient.

In some embodiments of the invention, the antihypertensive composition comprises a delivery medium, propionic acid and 3-methylpentanoic acid, the antihypertensive composition similarly adapted to induce at least 5-HT, secretin, prostaglandin E2 and vasoactive intestinal protein secretion in vivo, whereby, when the antihypertensive composition is delivered to a patient, vasodilation is induced.

In some embodiments, the antihypertensive composition further comprises butyrate.

In a preferred embodiment, the antihypertensive composition is similarly sufficient to induce at least 50% activation of at least olfactory receptor OR51E1, olfactory receptor OR51E2, free fatty acid receptor FFAR2, free fatty acid receptor FFAR3 and/or hydroxycarboxylic acid receptor GPR109A in vivo when the antihypertensive composition is delivered to a patient.

In some embodiments of the invention, there are also provided methods for treating hypertension comprising the steps of:
(a) providing one of the antihypertensive compositions of the invention; and
(b) delivering the antihypertensive compositions to a patient presenting with hypertension, whereby vasodilation is induced.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Before describing the present invention in detail, it is to be understood that this invention is not limited to particularly exemplified compounds, compositions or methods, as such may, of course, vary. Thus, although a number of compounds, compositions and methods similar or equivalent to those described herein can be used in the practice of the present invention, the preferred compounds, compositions and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a", "an" and "the" include plural referents unless the content clearly dictates otherwise. Thus, for example, reference to "an active agent" includes two or more such agents and the like.

Definitions

The term "hypertension" as used herein, means, and includes a systolic blood pressure greater than 130 mmHg and/or a diastolic blood pressure greater than 80 mmHg.

The terms "essential hypertension" and "primary hypertension" are also used collectively herein and mean, and include hypertension characterized by a systolic blood pressure greater than 130 mmHg or a diastolic blood pressure greater than 80 mmHg without a single, distinct underlying cause.

The terms "protein", "peptide", "polypeptide" and "polypeptide fragment" as used interchangeably herein, mean, and include amino acid polymers residues of any length. The amino acid polymer can be linear or branched, comprise modified amino acids or amino acid analogs, and it can be interrupted by chemical moieties other than amino acids. The terms "protein", "peptide", "polypeptide" and "polypeptide fragment" also include amino acid polymers that have been modified naturally or synthetically by chemical intervention; by way of example disulfide bond formation, glycosylation, lipidation, acetylation, phosphorylation, PEGylation or any other manipulation or modification, such as conjugation with a labeling or bioactive component.

The term "endocrine factor" as used herein, means, and includes any molecular compound that is produced and secreted by endogenous cells and induces biological activity at a biological tissue site. The term "endocrine factor" thus means and includes, without limitation, renin, prorenin, angiotensin I, angiotensin II, aldosterone, vasopressin (also referred to as antidiuretic hormone (ADH)), atrial natriuretic peptide (ANP), brain natriuretic peptide (BNP), nitric oxide, endothelin-1, dopamine, vascular endothelial growth factor (VEGF), basis fibroblast growth factor (bFGF), and erythropoietin (EPO).

The term "agonist" as used herein, means, and includes any molecule which binds to a receptor on a cell, wherein the binding to the receptor can potentially lead to subsequent changes in the cell's functions. When an agonist binds to a sufficient number of receptors, the receptors can activate seminal processes in the cell.

The term "antagonist", as used herein, means, and includes a molecule, which binds to a receptor on a cell and inhibits the receptor from activating processes in the cell. The inhibition of the receptor can include competitive binding against agonists (when an antagonist is bound agonists cannot bind to the receptor) and allosteric effects (when the antagonist binds agonists can still bind the receptor but cannot activate the receptor).

The term "G-protein coupled receptor (GPCR)", as used herein, means, and includes a transmembrane cell surface receptor that is adapted and configured to bind to extracellular molecules and induce cell signaling processes in response to the binding of the extracellular molecules. The term "G-protein coupled receptor (GPCR)" as used herein also, means, and includes olfactory receptors (including ectopic olfactory receptors), free fatty acid receptors and hydroxycarboxylic acid receptors.

The term "olfactory receptor (OR)" as used herein, means, and includes an olfactory receptor that is a seminal component of the chemosensory organs responsible for olfaction.

The term "olfactory receptor" as used herein, also means, and includes, trace amine associated receptors, vomeronasal receptors, formyl peptide receptors, membrane guanylyl cyclase, subtype GC-D receptors; and G-protein coupled receptors, such as G-protein coupled taste receptors. Olfactory receptors can also include hybrid receptors synthesized from the above-noted olfactory receptors.

The term "ectopic olfactory receptor", as used herein, means, and includes an olfactory receptor that is present in organs, tissue, and/or cells that is a seminal component of physiological processes outside of olfaction and, in some instances, indirectly involved with olfactory-mediated processes.

The term "free fatty acid receptor", as used herein, means and includes a transmembrane cell surface receptor that is adapted and configured to bind to fatty acids and induce cell signaling processes in response to the binding of the fatty acids.

The term "hydroxycarboxylic acid receptor", as used herein, means and includes a transmembrane cell surface receptor that is adapted and configured to bind to hydroxycarboxylic acids and induce cell signaling processes in response to the binding of the hydroxycarboxylic acids.

The term "compound", as used herein, means, and includes any composition of matter comprising two or more chemical elements. According to the invention, in some instances, the terms "compound" and "ligand" are synonymous and used interchangeably herein.

The term "compound" thus means and includes, without limitation, short chain fatty acids (SCFAs) (e.g., acetate, propionic acid, butyrate), 3-methylpentanoic acid, pentanoic acid, pentanol, 4-methylnonanoic acid, eugenol, farnesol, farnesyl thiosalicylic acid, acrolein, formalin, hydrogen peroxide, coumarin, dicyclohexyl disulfide, nonanoic acid, octanioic acid, 2-nonanoic acid, butyric acid, heptanoic acid, decanoic acid, tetradecanoic acid, trans-2-decenoic acid, tridecanoic acid, undecanoic acid, nicotinic acid, methyl eugenol, methyl salicylate, (+)-menthol, eugenyl acetate, 2,4-dinitrotoluene, 4-hydroxynonenal, hexanoic acid, 2-ethylhexanoic acid, 2-ethyl-3,5-dimethylpyrazine, pyrazine, dimethyl disulfide, methyl furfuryl disulfide, propanal, butyl butyryl lactate, isovaleric acid, propionic acid, 4-methylpentanoic acid, methanoic acid, octanoic acid, octanal, coumarin, helional, lilial, b-ionone, androstenone, androstadienone, caramel furanone, 3-phenyl propyl propionate, ethyl vanillin, 2-ethyl-fencol, N-amyl acetate, eugenol acetate, sandalwood, S-(−)-citronellol, (−)-citronellol, hydroxycitronellal, citral, S-(−)-citronellal, (+)-carvine, (−) carvone, (+) carvone, linalool, bourgeonal, acetophenone, amyl butyrate, nonanethiol, allyl phenyl acetate, N-amyl acetate, muscone, isoeugenol, eugenol methyl ether, heptanol, hexanol, hexyl acetate, 1-hexanol, 1-heptanol, 2-heptanone, octanol, 1-octanol, celery ketone, anis aldehyde, vanillin, guaiacol, hydroxymethylpentylcyclohexenecarboxaldehyde (lyral), allyl phenylacetate, allyl isothiocyanate, benzyl acetate, 3,4-hexanedione, cis-3-hexen-1-ol, quinoline, ethyl heptanoate, methyl octanoate, nonanal, 1-nonanol, 2-nonanol, 3-octanone, 3-nonanone, decyl aldehyde, (E)-non-2-enal 2-ethyl-3,5-dimethylpyrazine 3-methylbut-2-ene-1-thiol, (2E,6Z)-nona-2,6-dienalcitral, ethyl octanoate, p-mentha-8-thiol-3-one, β-myrcene, γ-decalactone, (S)-(+)-carvone, dihydrojasmone, cinnamaldehyde, spearmint, coffee difuran, quinoline, butyl anthranilate 2,2-dithiodimethylenedifuran, ethyl hexanoate, limonene, α-terpineol, eugenol (3E,5Z)-undeca-1,3,5-triene, long-chain free fatty acids (e.g., palmitic acid and stearic acid), medium-chain free fatty acids (e.g., caproic acid (C6:0), caprylic acid (C8:0), capric acid (C10:0), and lauric acid (C12:0)), and omega-3 polyunsaturated fatty acids (e.g., alpha-linoleic acid, docosahexaenoic acid and eicosatetraenoic acid).

The term "compound" also means and includes any composition of matter included in the Food and Drug Administration's (FDA's) generally recognized as safe (GRAS) database.

The terms "composition", "formulation", "olfactory composition" and "olfactory formulation", as used interchangeably herein, mean, and include any compound or combination of compounds that can interact with and modulate at least one receptor, such as a G-protein coupled receptor (e.g., an olfactory receptor and/or ectopic olfactory receptor and/or free fatty acid receptor and/or hydroxycarboxylic acid receptor).

The terms "olfaction" and "olfactory reception" as used interchangeably herein, mean, and include the interaction of a composition (or formulation) with an olfactory receptor coupled to a cell signaling pathway. The composition can also be defined as an "odorant" and may be airborne (i.e., volatile) and/or in solution.

The terms "express" and "expression" as used interchangeably herein, mean, and include the production of a protein product from the genetic information contained within a nucleic acid sequence.

The term "upregulation", as used herein, means, and includes the increased production of a protein product from the genetic information contained within a nucleic acid sequence.

The term "downregulation", as used herein, means, and includes the decreased production of a protein product from the genetic information contained within a nucleic acid sequence.

The terms "delivery" and "administration" are used interchangeably herein, and mean and include providing a composition (or formulation), through any method appropriate to deliver the composition (or formulation) to a subject.

According to the invention, such administration means includes, without limitation, oral, sublingual, inhalation, intranasal, epidural, intracerebral, transdermal, topical, and injection administration means.

The term "$EC_{50}$", as used herein, means and includes the concentration of a substance (e.g., a compound or a drug), which, after delivery to a subject, induces at least 50% activation or enhancement of a biological process.

In some embodiments, the term "$EC_{50}$" refers to the concentration of agonist which, after delivery to a subject, induces a response halfway between the baseline and maximum response in an in vitro assay.

In some embodiments, the term "$EC_{50}$" refers to the concentration of a modulator (e.g., an agonist) which, after delivery to a subject, induces at least 50% activation of a receptor type, by way of example, an ectopic olfactory receptor.

The term "$IC_{50}$", as used herein, means and includes the concentration of a substance (e.g., a compound or a drug), which, after delivery, inhibits or attenuates at least 50% of a biological process.

In some embodiments, the term "$IC_{50}$" refers to the concentration of a modulator (e.g., an antagonist or inhibitor), which, after delivery, inhibits or attenuates at least 50% of receptor activity, e.g., at least 50% of an ectopic olfactory receptor activity.

The term "comprise" and variations of the term, such as "comprising" and "comprises", means "including, but not limited to" and is not intended to exclude, for example, other compounds, ligands or method steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention.

As indicated above, the present invention is directed to compositions and methods for treating hypertension and hypertension-associated diseases and disorders by modulating receptor activity.

As discussed above, various entities have developed blood pressure reducing pharmaceutically active agents and therapies for treating hypertension by targeting seminal endocrine factors to reduce blood pressure to physiologically acceptable levels.

Although the pharmaceutically active agents can effectively reduce blood pressure, as also discussed in detail above, there are several drawbacks and disadvantages associated with administration of blood pressure reducing pharmaceutically active agents to patients, including, a myriad of side effects and difficulties calibrating the minimum effective dosages of multiple agents, when required.

As discussed in detail below, Applicant has developed compositions that directly and effectively modulate blood pressure, which overcome the drawbacks and disadvantages associated with conventional blood pressure reducing pharmaceutically active agents.

Although the compositions of the invention are described in connection with the treatment of hypertension; more particularly, the treatment of hypertensive endocrine diseases and disorders, and underlying causes thereof, use of the compositions is not limited solely to the treatment of hypertensive endocrine diseases and disorders. As will readily be appreciated by one having ordinary skill in the art, the compositions can also be employed to effectively treat additional diseases and/or disorders, including, without limitation, other cardiovascular diseases and disorders, reproductive diseases and disorders, immune diseases, and disorders, etc.

As discussed in detail below, in preferred embodiment, the compositions of the invention comprise at least one compound or ligand that is adapted to bind to and activate at least one G-protein coupled receptor (GPCR), e.g., an olfactory receptor and/or free fatty acid receptor and/or hydroxycarboxylic acid receptor, whereby vasodilation is induced, and blood pressure is reduced thereby (referred to herein as "antihypertensive compositions").

According to the invention, suitable compounds and ligands (also referred to herein as "GPCR activating compounds and ligands") that are adapted to bind to and activate at least one GPCR, whereby vasodilation is induced, include, without limitation, short chain fatty acids (SCFAs) (e.g., acetate, propionic acid, butyrate), 3-methylpentanoic acid, pentanoic acid, pentanol, 4-methylnonanoic acid, eugenol, farnesol, farnesyl thiosalicylic acid, acrolein, formalin, hydrogen peroxide, coumarin, dicyclohexyl disulfide, nonanoic acid, octanioic acid, 2-nonanoic acid, butyric acid, heptanoic acid, decanoic acid, tetradecanoic acid, trans-2-decenoic acid, tridecanoic acid, undecanoic acid, nicotinic acid, methyl eugenol, methyl salicylate, (+)-menthol, eugenyl acetate, 2,4-dinitrotoluene, 4-hydroxynonenal, hexanoic acid, 2-ethylhexanoic acid, 2-ethyl-3,5-dimethylpyrazine, pyrazine, dimethyl disulfide, methyl furfuryl disulfide, propanal, butyl butyryl lactate, isovaleric acid, propionic acid, 4-methylpentanoic acid, methanoic acid, octanoic acid, octanal, coumarin, helional, lilial, β-ionone, androstenone, androstadienone, caramel furanone, 3-phenyl propyl propionate, ethyl vanillin, 2-ethyl-fencol, N-amyl acetate, eugenol acetate, sandalwood, S-(−)-citronellol, (−)-citronellol, hydroxycitronellal, citral, S-(−)-citronellal, (+)-carvine, (−) carvone, (+) carvone, linalool, bourgeonal, acetophenone, amyl butyrate, nonanethiol, allyl phenyl acetate, N-amyl acetate, muscone, isoeugenol, eugenol methyl ether, heptanol, hexanol, hexyl acetate, 1-hexanol, 1-heptanol, 2-heptanone, octanol, 1-octanol, celery ketone, anis aldehyde, vanillin, guaiacol, hydroxymethylpentylcyclohexenecarboxaldehyde (lyral), allyl phenylacetate, allyl isothiocyanate, benzyl acetate, 3,4-hexanedione, cis-3-hexen-1-ol, quinoline, ethyl heptanoate, methyl octanoate, nonanal, 1-nonanol, 2-nonanol, 3-octanone, 3-nonanone, decyl aldehyde, (E)-non-2-enal 2-ethyl-3,5-dimethylpyrazine 3-methylbut-2-ene-1-thiol, (2E,6Z)-nona-2,6-dienalcitral, ethyl octanoate, p-mentha-8-thiol-3-one, β-myrcene, γ-decalactone, (S)-(+)-carvone, dihydrojasmone, cinnamaldehyde, spearmint, coffee difuran, quinoline, butyl anthranilate 2,2-dithiodimethylenedifuran, ethyl hexanoate, limonene, α-terpineol, eugenol (3E,5Z)-undeca-1,3,5-triene, long-chain free fatty acids (e.g., palmitic acid and stearic acid), medium-chain free fatty acids (e.g., caproic acid (C6:0), caprylic acid (C8:0), capric acid (C10:0), and lauric acid (C12:0)), and omega-3 polyunsaturated fatty acids (e.g., alpha-linoleic acid, docosahexaenoic acid and eicosatetraenoic acid).

According to the invention, the GPCR activating compounds and ligands (and, hence, compositions of the invention formed therefrom) are adapted to bind to and activate one or more of the following GPCRs: adipose olfactory receptors (e.g., OR51E2, OR2W3, OR51E1, OR2A1/42, OR2A4/7, OR52N4, OR13A1, 047D2, OR10J1, ORIL8, OR2B6, OR4D6, OLFR16, TASIR3, TAS2R10, TAS2R13, TAS2R14, TAS2R19, TAS2R20, TAS2R31, TAS2R40, TAS2R42, TAS2R5, VN1R1, and VN1R2), adrenal olfactory receptors (e.g., OR51E2, ORW3, OR51E1, OR2A1/42, OR2A4/7, OR52N4, OR13A1, OR5K2, OR3A2, OR2H$_2$, OR7C1, OR2L13, ORIL8, OR2T8, OR10AD1, OR52B6, OR1E1, OR13J1, OR2C1, OR52D1, OR10A2, OR2B6, OR8G5, OR1F12, OR4D6, TAS1R1, TAS1R3, TAS2R10, TAS2R13, TAS2R14, TAS2R19, TAS2R20, TAS2R3, TAS2R30, TAS2R31, TAS2R4, TAS2R42, TAS2R5, TAS2R50, TAS2R9, and VN1R1), central nervous system (CNS) olfactory receptors (e.g., OR51E2, OR2W3, OR4N4, OR51E1, OR52N4, OR13A1, OR5K2, OR7D2, OR3A2, OR2V1, OR2H$_2$, OR7C1, OR2L13, ORIL8, OR2T8, OR10AD1, OR3A3, OR2K2, OR13J1, OR2C1, OR7A5, OR10A2, OR1F12, TAAR3, TAAR5, TAAR6, TAS1R1, TAS1R3, TAS2R1, TAS2R10, TAS2R13, TAS2R14, TAS2R19, TAS2R20, TAS2R3, TAS2R30, TAS2R31, TAS2R39, TAS2R4, TAS2R40, TAS2R42, TAS2R46, TAS2R5, TAS2R50, TAS2R7, TAS2R8, TAS2R9, VN1R1, VN1R2, and VN1R5), dopaminergic neuron olfactory receptors (e.g., OR51E1, OR51E2, and OR2J3), mammary olfactory receptors (e.g., OR51E2, OR51E1, OR2A1/42, OR2A4/7, OR52N4, OR5K2, OR3A2, OR2T8, OR10AD1, OR3A3, OR2K2, OR1E1, OR2C1, OR2C3, OR8D1, OR7A5, OR10A2, TAS1R1, TAS1R3, TAS2R10, TAS2R13, TAS2R14, TAS2R19, TAS2R20, TAS2R31, TAS2R4, TAS2R5, and VN1R1), cardiovascular olfactory receptors (e.g., OR51E2, OR51E1, OR52N4, OR13A1, OR2H$_2$, OR10AD1, OR3A3, OR52B6, OR2K2, OR8G5, OR4D6, TAS1R1, TAS1R3, TAS2R10, TAS2R13, TAS2R14, TAS2R19, TAS2R20, TAS2R3, TAS2R30, TAS2R31, TAS2R4, TAS2R43, TAS2R46, TAS2R5, TAS2R50, TAS2R7, and VN1R1), renal olfactory receptors (e.g., OR51E2, OR51E1, OR2A1/42, OR2A4/7, OR5K2, ORIL8, OR10A2, OR1F12, TAS1R1, TAS1R3, TAS2R1, TAS2R10, TAS2R14, TAS2R19, TAS2R20, TAS2R3, TAS2R30, TAS2R31, TAS2R4, TAS2R42, TAS2R43, TAS2R5, TAS2R50, and VN1R1), hepatic olfactory receptors (e.g., OR2W3, OR51E1, OR2A1/42, OR2A4/7, OR7D2, ORIL8, OR2T8. TAS1R3, TAS2R14, TAS2R14, TAS2R20, TAS2R30, TAS2R30, TAS2R40, TAS2R5, VN1R1, and VN1R2), lymphatic olfactory receptors (e.g., OR51E2, OR51E1, OR2W3, OR2A1/42, OR2A4/7, OR52N4, OR13A1, OR5K2, OR7D2, OR3A2, OR2H$_2$, OR3A3, OR2B6, OR52B6, TAS1R3, TAS2R14, TAS2R19, TAS2R20, TAS2R31, TAS2R4, TAS2R5, TAS2R40, TAS2R50, TAS2R43, TAS2R5 and VN1R1), ovarian olfactory receptors (e.g., OR51E2, OR2W3, OR4N4, OR51E1, OR2A1/42, OR2A4/7, OR52N4, OR5K2, OR3A2, OR2V1, OR2H$_2$, OR2L13, ORIL8, OR10AD1, OR3A3, OR52B6, OR13J1, OR2C1, OR52D1, OR51B5, OR1F12, TAS1R1, TAS1R3, TAS2R1, TAS2R10, TAS2R13, TAS2R14, TAS2R19, TAS2R20, TAS2R3, TAS2R31, TAS2R4, TAS2R42, TAS2R43, TAS2R5, TAS2R50, TAS2R60, TAS2R7, VN1R1, and VN1R2), prostate olfactory receptors (e.g., OR51E2, OR2W3, OR51E1, OR2A1/42, OR2A4/7, OR52N4, OR13A1, OR5K2, OR2H$_2$, OR7C1, OR1E1, OR13J1, OR51B5, TAS1R3, TAS2R14, TAS2R19, TAS2R20, TAS2R43, TAS2R46, TAS2R5, and VN1R1), dermal olfactory receptors (e.g., OR2AT4), testicular olfactory receptors (e.g., OR4N4, OR6F1, OR2H$_1$, OR51E2, OR2W3, OR4N4, OR51E1, OR2A1/42, OR2A4/7, OR52N4, OR7D2, OR3A2, OR2V1, OR2H$_2$, OR7C1, OR10J1, ORIL8, OR1C1, OR2H$_1$, OR10AD1, OR3A3, OR13C3, OR2K2, OR1E1, OR2C1, OR2K2, OR1E1, OR2C1, OR2C3, OR8D1, OR52D1, OR7A5, OR10A2, OR2B6, OR7E24, OR6F1, OR8G5, OR51B5, OR1F12, TAS1R1, TAS1R3, TAS2R1, TAS2R14, TAS2R19, TAS2R20, TAS2R3, TAS2R31, TAS2R4, TAS2R43, TAS2R5, TAS2R50 TAS2R60, VN1R1, VN1R2, VN1R3, and VN1R4), hematologic olfactory receptors (e.g., OR2W3, OR2A4/7, OR52N4, OR7D2, OR2L13, OR3A3, OR2C1, OR2C3, OR2B6, TAS1R3, TAS2R14, TAS2R20, TAS2R40, and TAS2R60), free fatty acid receptors (e.g., FFAR1, FFAR2, FFAR3, and FFAR4), hydroxycarboxylic acid receptors (e.g., hydroxycarboxylic acid receptor 2 (HCA$_2$ (also referred to herein as GPR109A)), hydroxycarboxylic acid receptor 3 (HCA$_3$ (or also referred to herein as GPR109B)), and hydroxycarboxylic acid receptor 1 (HCA$_1$ (also referred to herein as GPR81))), and trace amine-associated receptors (e.g., TAAR1, TAAR2, TAAR3, TAAR4P, TAAR5, TAAR6, TAAR7P, TAAR8, and TAAR9).

Other ectopic olfactory receptors found in other tissues, organs and cells, which the GPCR activating compounds and ligands (and, hence, compositions of the invention formed therefrom) are adapted to bind to and activate, are described in U.S. application Ser. Nos. 15/927,083 and 17/048,059, which are incorporated by reference in their entirety for all purposes described herein.

As indicated above and described in detail herein, in some embodiments of the invention, the GPCR activating compounds and ligands of the invention referenced above and, hence, compositions of the invention formed therefrom are adapted to bind to and activate combinations of the aforementioned receptors, e.g., multiple receptors.

G-Protein Coupled Receptor (GPCR)-Mediated Vasodilation

As indicated above, in preferred embodiment of the invention, the antihypertensive compositions of the invention comprise at least one compound or ligand that is adapted to bind to and activate at least one G-protein coupled receptor (GPCR), whereby vasodilation is induced.

In a preferred embodiment, the "target" GPCRs comprise olfactory receptor family 51 subfamily E member 2 (OR51E2), olfactory receptor family 51 subfamily E member 1 (OR51E1), free fatty acid receptor 3 (FFAR3), free fatty acid receptor 2 (FFAR2) and hydroxycarboxylic acid receptor 2 (GPR109A).

In some embodiments of the invention, the GPCR activating compounds and ligands, and antihypertensive compositions of the invention formed therefrom are specifically adapted to bind to and activate at least one olfactory receptor including, without limitation, olfactory receptor OR51E2 and olfactory receptor OR51E1, whereby vasodilation is induced.

In some embodiments of the invention, the GPCR activating compounds and ligands, and antihypertensive compositions of the invention formed therefrom are specifically adapted to bind to and activate at least one free fatty acid receptor including, without limitation, free fatty acid receptor FFAR3 and free fatty acid receptor FFAR2, whereby vasodilation is induced.

In some embodiments of the invention, the receptor activating compounds and ligands, and antihypertensive compositions of the invention formed therefrom are specifically adapted to bind to and activate at least one hydroxycarboxylic acid receptor including, without limitation, hydroxycarboxylic acid receptor GPR109A, whereby vasodilation is induced.

According to the invention, the noted antihypertensive compositions of the invention, when delivered to a patient, effectuate the following highly effective and, hence, desirable pharmacodynamic activity.

Figure 1:
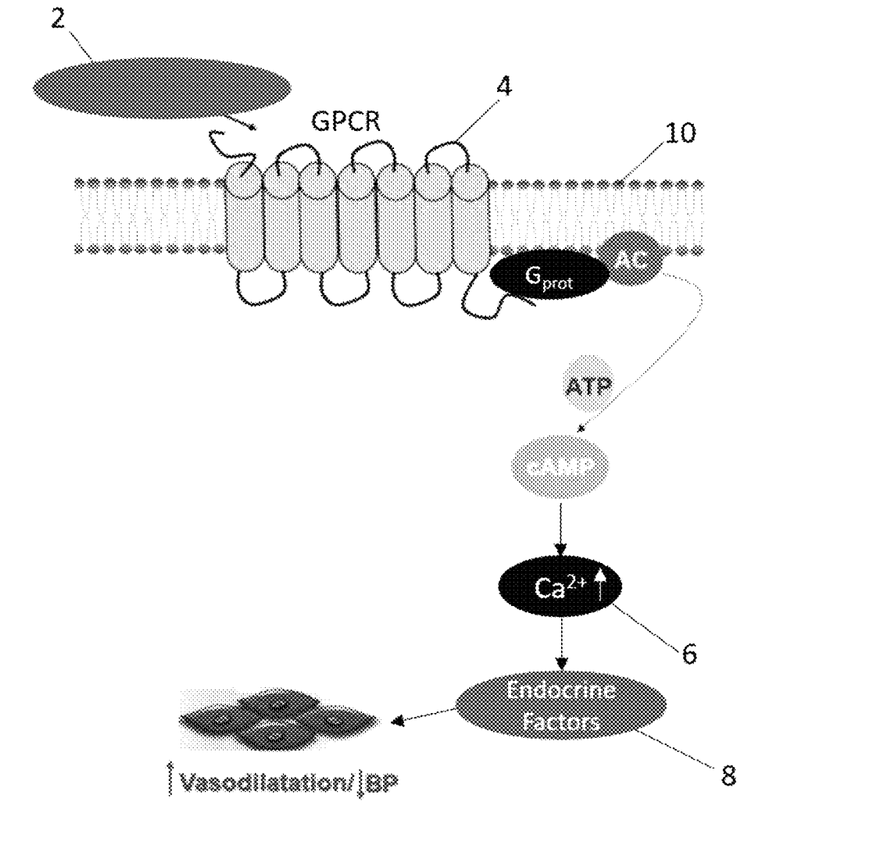
FIG. 1 is a schematic illustration of G-protein coupled receptor-mediated cell signaling modulation of vasodilation by endogenous cells.

Referring now to FIG. 1, in a preferred embodiment, the antihypertensive compositions of the invention (denoted "2") target and bind to G-protein coupled receptors (GPCRs)

(e.g., olfactory receptors (ORs), free fatty acid receptors (FFARs), and hydroxycarboxylic acid receptors (HCAs)) (denoted "4"), disposed on endogenous cells (denoted "10"), such as afferent arteriole isolated juxtaglomerular granular (JG) cells and vascular endothelial cells. The binding of the compositions to the GPCRs induces activation of at least one G-Protein (denoted "$G_{prot}$") leading to increased cyclic adenosine monophosphate (cAMP) via synthesis of cAMP from ATP by adenylate cyclases (ACs), which results in glucose-induced membrane depolarization of the endogenous cells.

(VEGF), basis fibroblast growth factor (bFGF), and erythropoietin (EPO) via activation of the target GPCRs of the invention.

The antihypertensive compositions of the invention thus provide a highly effective means of treating adverse hypertensive endocrine responses and, hence, hypertensive endocrine diseases and disorders associated therewith via activation of target GPCRs of the invention.

In a preferred embodiment, the antihypertensive compositions of the invention thus comprise at least one of the GPCR activating compounds listed below in Table I below.

TABLE I

| GPCR | Expression Site | Compounds/Ligands | Signaling Pathway | Biological Process |
|---|---|---|---|---|
| OR51E2 | Vascular Smooth Muscle Cells Juxtaglomerular Granular (JG) Cells | Propionic Acid Acetate β-Ionone | cAMP-Mediated | Vasodilation and Reduced Blood Pressure |
| OR51E1 | Renal Cells Myocardial Cells Retinal Cells Vascular Smooth Muscle Cells | Butyrate Isovaleric Acid 3-Methylpentanoic Acid Eugenol Farnesol Nonanoic Acid | cAMP-Mediated | Vasodilation and Reduced Blood Pressure |
| FFAR3 | Vascular Endothelial Cells | Butyrate Propionic Acid Acetate | cAMP-Mediated | Vasodilation and Reduced Blood Pressure |
| FFAR2 | Vascular Smooth Muscle Cells Immune Cells, e.g., Macrophages | Butyrate Propionic Acid Acetate | cAMP-Mediated | Vasodilation and Reduced Blood Pressure |
| GPR109A/HCA$_2$ | Renal Podocytes Immune Cells, e.g., Macrophages | Butyrate Nicotinic Acid | cAMP-Mediated | Vasodilation and Reduced Blood Pressure |

The glucose-induced membrane depolarization of the endogenous cells opens the voltage-dependent $Ca^{2+}$ (VDC) channels of the cells, and the resulting $Ca^{2+}$ influx (denoted "6") triggers vesicular exocytosis and increases secretion of vasodilation inducing endocrine factors (denoted "8") from the cells. The secreted endocrine factors induce activation of cell signaling pathways that induce vasodilation and activation of other seminal physiological processes that reduce blood pressure.

The secreted vasodilation inducing endocrine factors typically comprise serotonin (5-HT), secretin, prostaglandin E2, and vasoactive intestinal protein, which induce vasodilation and/or modulate BP by inducing smooth muscle relaxation and stimulating the elimination of water from the body, which all contribute to a reduction of BP.

Thus, in a preferred embodiment, activation of target GPCRs of the invention, i.e., olfactory receptor OR51E2, olfactory receptor OR51E1, free fatty acid receptor FFAR2, free fatty acid receptor FFAR3 and hydroxycarboxylic acid receptor GPR109A, by the antihypertensive compositions of the invention thus induces secretion of at least one of the aforementioned "vasodilation inducing" endocrine factors.

According to the invention, the antihypertensive compositions of the invention can also effectuate secretion modulation, i.e., increase or abate secretion, of the following additional endocrine factors: renin, prorenin, angiotensin I, angiotensin II, aldosterone, vasopressin (also referred to as antidiuretic hormone (ADH)), atrial natriuretic peptide (ANP), brain natriuretic peptide (BNP), nitric oxide, endothelin-1, dopamine, vascular endothelial growth factor As indicated above, in a preferred embodiment, the antihypertensive compositions of the invention comprise at least one of the GPCR activating compounds listed in Table I. In some embodiments of the invention, discussed below, the antihypertensive compositions of the invention comprise combinations of the compounds listed in Table I.

As also indicated above, in some embodiments of the invention, the antihypertensive compositions of the invention are preferably adapted to activate at least one of the following olfactory receptors: OR51E2 and OR51E1. Modulation of the noted receptors and the desirable pharmacodynamic activity resulting therefrom is described below.

OR51E2 Modulation

In some embodiments of the invention, the antihypertensive compositions of the invention thus comprise one or more GPCR activating compounds and/or ligands that are specifically adapted to activate OR51E2 (also referred to herein as "OR51E2 modulation compositions").

As indicated above, activation of OR51E2 induces activation of at least one G-protein, in this instance $G_{olf/stim}$, which results in increased cyclic adenosine monophosphate (cAMP) production via synthesis of cAMP from ATP by adenylate cyclases (ACs) and glucose-induced membrane depolarization of endogenous cells, such as vascular smooth muscle cells and JG cells.

The glucose-induced membrane depolarization of the endogenous cells opens the voltage-dependent $Ca^{2+}$ (VDC) channels of the cells, and the resulting $Ca^{2+}$ influx induces vesicular exocytosis and increases secretion of vasodilation inducing endocrine factors from the cells. The secreted endocrine factors induce activation of cell signaling pathways that induce vasodilation and other seminal physiological processes that reduce blood pressure.

As also indicated above, the secreted vasodilation inducing endocrine factors typically comprise 5-HT, secretin, prostaglandin E2 and vasoactive intestinal protein.

In a preferred embodiment, activation of OR51E2 thus at least induces secretion of at least one of the referenced vasodilation inducing endocrine factors.

According to the invention, activation of OR51E2 can also effectuate secretion modulation, i.e., increase or abate secretion, of the additional aforementioned endocrine factors.

As indicated above, the antihypertensive compositions of the invention can comprise a single GPCR activating compound or ligand, which is adapted to bind to and activate OR51E2.

As also indicated above, the antihypertensive compositions of the invention can also comprise a combination of GPCR activating compounds and/or ligands, which are similarly adapted to bind to and activate at least OR51E2.

In some embodiments of the invention, the antihypertensive compositions of the invention thus comprise at least one of the following GPCR activating compounds, which, as indicated above, are adapted to activate OR51E2, whereby vasodilation is induced: propionic acid, acetate and β-ionone.

In some embodiments, the antihypertensive compositions comprise propionic acid, acetate and β-ionone.

Each of the noted GPCR activating compounds and the pharmacodynamic activity induced thereby is summarized below.

Propionic Acid

As is well established, propionic acid is a naturally occurring short chain fatty acid (SCFA) with the chemical formula $CH_3CH_2CO_2H$ that is produced by microbial fermentation of dietary carbohydrates in the gastrointestinal system. Propionic acid is a liquid with a pungent and unpleasant smell that is similar to the smell of human body odor.

Applicant has found that when propionic acid binds to a GPCR; particularly, OR51E2, the propionic acid induces a conformational change in the molecular structure of OR51E2 that induces the binding of OR51E2 to at least $G_{olf/stim}$, thereby, activating cyclic adenosine monophosphate (cAMP), which results in an increase in intracellular cAMP levels.

As indicated above, the intracellular cAMP molecules activate the opening of cyclic nucleotide gated channels that allow $Ca^{2+}$ to enter an endogenous cell (such as a vascular smooth muscle cell), which leads to depolarization of the cell and initiation of an action potential. As discussed in detail above, activation of an olfactory receptor, in this instance, OR51E2 induces vasodilation and an attendant reduction in blood pressure.

Acetate

Acetate is another short chain fatty acid with the chemical formula $CH 3CO_2$, that is similarly produced by microbial fermentation of dietary carbohydrates in the gastrointestinal system. Acetate is also a liquid with a pungent vinegary smell.

Applicant has found that when acetate binds to an olfactory receptor, such as OR51E2, the acetate induces a conformational change in the molecular structure of OR51E2 that is substantially similar to the conformational change induced by propionic acid and, thus, also induces vasodilation and an attendant reduction in blood pressure.

β-Ionone

β-ionone is a member of a closely related family of chemical compounds that are commonly referred to as "rose ketones," which includes damascones and damascenones. β-ionone is a liquid compound that is a significant contributor to the aroma of roses and violets.

Applicant has found that when β-ionone binds to an olfactory receptor, such as OR51E2, the β-ionone induces a conformational change in the molecular structure of OR51E2 that is substantially similar to the confirmational change induced by propionic acid and, thus, also induces vasodilation and an attendant reduction in blood pressure.

As indicated above, the antihypertensive compositions of the invention preferably comprise one or more of the following GPCR activating compounds, which are adapted to activate OR51E2, whereby vasodilation is induced: propionic acid, acetate and β-ionone.

According to the invention, the $EC_{50}$ values of the noted GPCR (or OR51E2) activating compounds in an antihypertensive composition of the invention can comprise any $EC_{50}$ values or $EC_{50}$ value ranges in the range of approximately 1.0 nM to approximately 200.0 mM.

Thus, according to the invention, the $EC_{50}$ values of the noted GPCR (or OR51E2) activating compounds in an antihypertensive composition of the invention can comprise in the range of approximately 0.001 μM to approximately 100,000.0 μM, approximately 0.002 UM to approximately 10,000.0 μM, approximately 0.003 μM to approximately 1,000.0 μM, approximately 0.005 μM to approximately 750.0 μM, approximately 0.01 M to approximately 500.0 μM, approximately 0.1 μM to approximately 50.0 μM, approximately 0.05 μM to approximately 400.0 μM, approximately 0.1 μM to approximately 350.0 μM, approximately 0.5 μM to approximately 300.0 μM, approximately 1.0 μM to approximately 200.0 μM, approximately 1.0 μM to approximately 100.0 μM, approximately 1.0 μM to approximately 50.0 μM, approximately 2.5 μM to approximately 100.0 μM, approximately 5.0 μM to approximately 75.0 μM, approximately 7.5 μM to approximately 50.0 μM, approximately 10.0 μM to approximately 25.0 μM, and/or any $EC_{50}$ values therebetween.

According to the invention, the $EC_{50}$ values of the noted GPCR (or OR51E2) activating compounds in an antihypertensive composition of the invention can also comprise in the range of approximately 0.001 μM to approximately 10.0 μM, approximately 0.005 μM to approximately 7.5 μM, approximately 0.01 μM to approximately 5.0 μM, approximately 0.03 μM to approximately 2.5 μM, approximately 0.05 μM to approximately 1.5 μM, approximately 0.03 μM to approximately 1.0 μM, approximately 0.1 μM to approximately 0.5 μM, and/or any $EC_{50}$ values therebetween.

In some embodiments, the $EC_{50}$ values of the noted GPCR (or OR51E2) activating compounds in the antihypertensive composition of the invention comprise at least 0.001 μM, at least 0.002 μM, at least 0.003 μM, at least 0.004 μM, at least 0.005 μM, at least 0.006 μM, at least 0.007 μM, at least 0.008 μM, at least 0.009 μM, at least 0.01 μM, at least 0.02 μM, at least 0.03 μM, at least 0.04 μM, at least 0.05 μM, at least 0.06 μM, at least 0.07 μM, at least 0.08 μM, at least 0.09 μM, at least 0.1 μM, at least 0.2 μM, at least 0.3 μM, at least 0.4 μM, at least 0.5 μM, at least 0.6 μM, at least 0.7 μM, at least 0.8 μM, at least 0.9 μM, at least 1.0 μM, at least 2.0 μM, at least 3.0 μM, at least 4.0 μM, at least 5.0 μM, at least 6.0 μM, at least 7.0 μM, at least 8.0 μM, at least 9.0 μM, at least 10.0 μM, at least 20.0 μM, at least 30.0 μM, at least 40.0 μM, at least 50.0 μM, at least 60.0 μM, at least 70.0 μM, at least 80.0 μM, at least 90.0 μM, at least 100.0 μM, 200.0

μM, at least 300.0 μM, at least 400.0 M, at least 500.0 μM, at least 600.0 μM, at least 700.0 μM, at least 800.0 μM, at least 900.0 μM, or at least 1,000.0 μM.

In some embodiments, the $EC_{50}$ value of propionic acid in the noted antihypertensive composition comprises an $EC_{50}$ value in the range of approximately 6.0 μM to approximately 127.0 μM.

In a preferred embodiment, the $EC_{50}$ value of propionic acid in the noted antihypertensive composition comprises in the range of approximately 0.05 μM to approximately 0.5 μM, more preferably, in the range of approximately 0.1 μM to approximately 0.2 μM.

In some embodiments, the $EC_{50}$ value of acetate in the noted antihypertensive composition, comprises an $EC_{50}$ value in the range of approximately 1.0 μM to approximately 200.0 μM more preferably, in the range of approximately 50.0 μM to approximately 125.0 μM.

In a preferred embodiment, the $EC_{50}$ value of acetate in the noted antihypertensive composition comprises in the range of approximately 0.01 μM to approximately 0.3 μM, more preferably, in the range of approximately 0.01 μM to approximately 0.02 μM.

In some embodiments, the $EC_{50}$ value of β-ionone in the noted antihypertensive composition comprises in the range of approximately 1.0 μM to approximately 200.0 μM more preferably, in the range of approximately 50.0 μM to approximately 125.0 μM.

In a preferred embodiment, the $EC_{50}$ value of β-ionone in the antihypertensive composition comprises in the range of approximately 10.0 μM to approximately 100 μM.

OR51E1 Modulation

In some embodiments, the antihypertensive compositions of the invention comprise one or more GPCR activating compounds and/or ligands that are specifically adapted to activate OR51E1 whereby, pharmacodynamic activity similar to that induced via activation of OR51E2 (discussed above) is induced (also referred to herein as "OR51E1 modulation compositions").

According to the invention, the antihypertensive compositions of the invention can thus comprise one or more of the following GPCR activating compounds, which are adapted to activate OR51E1, whereby vasodilation is similarly induced: butyrate, isovaleric acid, 3-methylpentanoic acid, eugenol, farnesol, and nonanoic acid.

According to the invention, the $EC_{50}$ value of the above noted GPCR (or OR51E1) activating compounds in an antihypertensive composition of the invention can similarly comprise any of the aforementioned $EC_{50}$ value ranges and $EC_{50}$ values therebetween.

In some embodiments, the $EC_{50}$ value of butyrate in the noted antihypertensive composition comprises an $EC_{50}$ value in the range of approximately 0.1 μM to approximately 200.0 μM more preferably, in the range of approximately 50.0 μM to approximately 125.0 μM.

In a preferred embodiment, the $EC_{50}$ value of butyrate in the noted antihypertensive composition comprises in the range of approximately 0.01 μM to approximately 0.3 μM, more preferably, in the range of approximately 0.01 μM to approximately 0.02 μM.

In some embodiments, the $EC_{50}$ value of isovaleric acid in the noted antihypertensive composition comprises in the range of approximately 4.0 mM to approximately 21.0 mM.

In a preferred embodiment, the $EC_{50}$ value of isovaleric acid in the noted antihypertensive composition comprises in the range of approximately 0.1 μM to approximately 200.0 M, more preferably, in the range of approximately 1.0 μM to approximately 100.0 μM.

In a preferred embodiment, the $EC_{50}$ value of 3-methylpentanoic acid in the noted antihypertensive composition comprises in the range of approximately 5.0 M to approximately 50.0 μM, more preferably, in the range of approximately 10.0 μM to approximately 30.0 μM.

In a preferred embodiment, the $EC_{50}$ value of eugenol in the noted antihypertensive composition comprises in the range of approximately 0.5 μM to approximately 20.0 μM, more preferably, in the range of approximately 1.0 μM to approximately 15.0 μM.

In a preferred embodiment, the $EC_{50}$ value of farnesol in the noted antihypertensive composition comprises in the range of approximately 0.1 μM to approximately 10.0 μM, more preferably, in the range of approximately 0.4 μM to approximately 0.5 μM.

In a preferred embodiment, the $EC_{50}$ value of nonanoic acid in the noted antihypertensive composition comprises in the range of approximately 0.05 μM to approximately 0.4 μM, more preferably, in the range of approximately 0.1 μM to approximately 0.2 μM.

FFAR3 Modulation

In some embodiments, the antihypertensive compositions of the invention comprise one or more GPCR activating compounds and/or ligands that are specifically adapted to activate FFAR3 whereby, the following pharmacodynamic activity is induced (also referred to herein as "FFAR3 modulation compositions").

According to the invention, activation of FFAR3 induces a conformational change in the molecular structure of FFAR3, whereby intracellular $G_\alpha/G_\beta/G_\gamma$ subunits of FFAR3 act as a guanine nucleotide exchange factor and, thus, exchange a guanine diphosphate (GDP) for a guanine triphosphate (GTP), which binds to the Ga subunit of FFAR3. The noted binding of the GTP to the Ga subunit then induces a dissociation of the $G_\alpha/G_\beta/G_\gamma$ subunits of FFAR3 into a free $G_\alpha$ subunit and $G_\beta/G_\gamma$ complex, which activates seminal downstream cell signaling processes that induce an increase in intracellular cAMP in endogenous cells, such as vascular endothelial cells.

The intracellular cAMP level increase induces opening of cyclic nucleotide gated $Ca^{2+}$ channels, which results in increased cellular $Ca^{2+}$. The increased cellular $Ca^{2+}$ induces vesicular exocytosis and similarly increases secretion of vasodilation inducing endocrine factors from the cells. The secreted vasodilation inducing endocrine factors similarly induce activation of cell signaling pathways that induce vasodilation and activation of other seminal physiological processes that reduce blood pressure.

The secreted vasodilation inducing endocrine factors comprise L-glutamate and 5-HT.

In a preferred embodiment, activation of FFAR3 thus at least induces secretion of at least one of the referenced vasodilation inducing endocrine factors.

According to the invention, activation of FFAR3 can also effectuate secretion modulation, i.e., increase or abate secretion, of the additional aforementioned endocrine factors.

As indicated below, according to the invention, the antihypertensive compositions of the invention can comprise a single GPCR activating compound (or ligand), which is adapted to bind to and activate FFAR3.

As also indicated above, the antihypertensive compositions of the invention can also comprise a combination of GPCR activating compounds (and/or ligands), which are similarly adapted to bind to and activate at least FFAR3.

According to the invention, the antihypertensive compositions of the invention can thus comprise one or more of the following GPCR activating compounds, which, as indicated above, are adapted to activate FFAR3, whereby vasodilation is similarly induced: butyrate, propionic acid and acetate.

In some embodiments, the antihypertensive compositions of the invention comprise butyrate, propionic acid and acetate.

According to the invention, the $EC_{50}$ value of the above noted GPCR (or FFAR3) activating compounds in an antihypertensive composition of the invention can similarly comprise any of the aforementioned $EC_{50}$ value ranges and $EC_{50}$ values therebetween.

In a preferred embodiment, the $EC_{50}$ value of butyrate in the noted antihypertensive composition comprises in the range of approximately 0.01 µM to approximately 0.3 µM, more preferably, in the range of approximately 0.01 µM to approximately 0.02 µM.

In a preferred embodiment, the $EC_{50}$ value of propionic acid in the noted antihypertensive composition comprises in the range of approximately 0.05 µM to approximately 0.5 µM, more preferably, in the range of approximately 0.1 µM to approximately 0.2 µM.

In a preferred embodiment, the $EC_{50}$ value of acetate in the noted antihypertensive composition comprises in the range of approximately 0.01 µM to approximately 0.3 µM, more preferably, in the range of approximately 0.01 µM to approximately 0.02 µM.

FFAR2 Modulation

In some embodiments, the antihypertensive compositions of the invention comprise one or more GPCR activating compounds and/or ligands that are specifically adapted to activate FFAR2 whereby, pharmacodynamic activity similar to that induced via activation of FFAR3 (discussed above) is induced (also referred to herein as "FFAR2 modulation compositions").

According to the invention, the antihypertensive compositions of the invention can thus similarly comprise butyrate and/or propionic acid and/or acetate.

According to the invention, the $EC_{50}$ value of the above noted GPCR (or FFAR2) activating compounds in an antihypertensive composition of the invention can similarly comprise any of the aforementioned $EC_{50}$ value ranges and $EC_{50}$ values therebetween.

GPR109A Modulation

In some embodiments, the antihypertensive compositions of the invention comprise one or more GPCR activating compounds and/or ligands that are specifically adapted to activate GPR109A, whereby pharmacodynamic activity similar to that induced via activation of FFAR3 (discussed above) is induced (also referred to herein as "GPR109A modulation compositions").

It has been found and Applicant has confirmed that the activation of GPR109A attenuates the production and release of endogenous nuclear factor κ-B (NK-κB), NADPH Oxidases (NOXs), and renin, and, thereby, reduces blood pressure and, hence, treats hypertension.

In a preferred embodiment, activation of GPR109A also modulates secretion of at least one of the above referenced vasodilation inducing endocrine factors.

As indicated below, according to the invention, the antihypertensive compositions of the invention can comprise a single GPCR activating compound (or ligand), which is adapted to bind to and activate GPR109A.

As also indicated above, the antihypertensive compositions of the invention can also comprise a combination of GPCR activating compounds (and/or ligands), which are similarly adapted to bind to and activate at least GPR109A.

According to the invention, the antihypertensive compositions of the invention can thus comprise one or more of the following GPCR activating compounds, which, as indicated above, are adapted to activate GPR109A, whereby vasodilation is similarly induced: butyrate and nicotinic acid.

According to the invention, the $EC_{50}$ value of the above noted GPCR (or GPR109A) activating compounds in an antihypertensive composition of the invention can similarly comprise any of the aforementioned $EC_{50}$ value ranges and $EC_{50}$ values therebetween.

In a preferred embodiment, the $EC_{50}$ value of butyrate in the noted antihypertensive composition comprises in the range of approximately 0.01 µM to approximately 0.3 µM, more preferably, in the range of approximately 0.01 µM to approximately 0.02 µM.

In a preferred embodiment, the $EC_{50}$ value of nicotinic acid in the noted antihypertensive composition comprises in the range of approximately 0.05 µM to approximately 0.5 µM, more preferably, in the range of approximately 0.1 µM to approximately 0.2 µM.

In some embodiments, modulating the activity of multiple receptors, e.g., olfactory receptors and/or free fatty acid receptors and/or hydroxycarboxylic acid receptors, as described herein, results in elevated endocrine factor levels.

In some embodiments, modulating the activity of multiple receptors, e.g., olfactory receptors and/or free fatty acid receptors and/or hydroxycarboxylic acid receptors, as described herein, results in synergistically elevated endocrine factor levels.

In some embodiments, modulating the activity of multiple receptors, e.g., olfactory receptors and/or free fatty acid receptors and/or hydroxycarboxylic acid receptors, as described herein, results in elevated endocrine factor secretion.

In some embodiments, modulating the activity of multiple receptors, e.g., olfactory receptors and/or free fatty acid receptors and/or hydroxycarboxylic acid receptors, as described herein, results in synergistically elevated endocrine factor secretion.

In some embodiments, modulating the activity of multiple receptors, e.g., olfactory receptors and/or free fatty acid receptors and/or hydroxycarboxylic acid receptors, as described herein, results in endocrine factor secretion higher than endocrine factor secretion induced when modulating the activity of any single receptor alone.

In some embodiments, modulating the activity of multiple receptors, e.g., olfactory receptors and/or free fatty acid receptors and/or hydroxycarboxylic acid receptors, as described herein, induces a beneficial biological response, including, by way of example, decreased systolic blood pressure, decreased diastolic pressure, decreased mean arterial pressure, improved ejection fraction, improved stroke volume, and improved end-diastolic volume than when modulating the activity of any single receptor alone.

In some embodiments, the compositions of the invention further comprise a physiologically suitable (or acceptable) carrier (also referred to herein as a physiologically suitable (or acceptable) excipient, or physiologically suitable (or acceptable) excipient selected based on a chosen route of administration, e.g., oral administration, and standard pharmaceutical practice.

According to the invention, suitable aqueous and non-aqueous carriers that can be employed in the compositions of the invention include water, ethanol, polyols (such as glycerol, glycerin-based water, propylene glycol, polyethylene glycol, and the like), and suitable mixtures thereof; vegetable oils, such as olive oil; buffers such as neutral buffered saline, phosphate buffered saline and the like; carbohydrates, such as glucose, mannose, sucrose, and dextran, mannitol; proteins; polypeptides, and amino acids, such as glycine; antioxidants; chelating agents such as ethylenediaminetetraacetic acid (EDTA) or glutathione; adjuvants (e.g., aluminum hydroxide); and injectable organic esters, such as ethyl oleate and cyclodextrins.

According to the invention, the compositions can be manufactured by means of conventional mixing, dissolving, granulating, dragee-making, levigating, emulsifying, encapsulating, entrapping, and lyophilizing processes. The manufactured compositions can take the form of solutions, suspensions, emulsion, tablets, pills, pellets, capsules, capsules containing liquids, powders, sustained-release formulations, suppositories, emulsions, aerosols, sprays, suspensions, and other forms suitable for administration to a patient.

In some embodiments, proper fluidity of a composition is maintained via coating materials, such as lecithin.

According to the invention, the compositions of the invention can be formulated into any known form suitable for parenteral administration, e.g., injection or infusion. Alternatively, the compositions can be formulated for oral administration, nasal or other mucosal tissue administration, or administration as a suppository (e.g., for small molecules). The compositions can also comprise formulation additives, such as suspending agents, preservatives, stabilizers and/or dispersants, and preservation agents.

According to the invention, the compositions can thus be administered to a patient via any suitable method, including, without limitation, oral, sublingual, inhalation, intranasal, epidural, intracerebral, transdermal, topical, and injection administration means.

The compositions of the invention can also be administered to a patient via intraarterial, subcutaneous, intradermal, intratumoral, intranodal, intramedular, intramuscular, intranasally, and intraperitoneal means.

According to the invention, the compositions of the invention can also be incorporated into various ingestible fluids, such as flavored waters and coffee.

According to the invention, the compositions of the invention can also be incorporated into a food item, such as a cracker, and/or a nutritional supplement or supplemental food item, such as protein bar.

In some embodiments, the compositions of the invention are administered at a dosage of from about 50.0 mg/kg to about 10.0 g/kg, from about 100.0 µg/kg to about 50.0 mg/kg, from about 1.0 mg/kg to about 50.0 mg/kg, and in certain embodiments, from about 5.0 mg/kg to about 25.0 mg/kg, including all integer values within those ranges.

In some embodiments, the compositions are administered at a dose over time from about 1.0 mg to about 5.0 g per day, from about 10.0 mg to about 4.0 g per day, and in certain embodiments, from about 20.0 mg to about 2.0 g per day, including all integer values within those ranges. According to the invention, compositions can also be administered multiple times per day at these dosages.

According to the invention, the noted dosages and delivery protocols are sufficient to induce sustained (i.e., extended periods) of vasodilation and, hence, a reduction in blood pressure to physiologically acceptable levels.

As indicated above, there are thus provided several antihypertensive compositions for treating hypertension and hypertension-associated diseases and disorders.

In one embodiment of the invention, the antihypertensive composition comprises a delivery medium, propionic acid and butyrate, the propionic acid comprising an $EC_{50}$ value in the range of from about 0.05 µM to about 0.5 M, the butyrate comprising an $EC_{50}$ value in the range of from about 0.01 µM to about 0.3 µM, the antihypertensive composition adapted to induce at least serotonin (5-HT), secretin, prostaglandin E2 and vasoactive intestinal protein secretion in vivo, whereby, when the antihypertensive composition is delivered to a patient, vasodilation is induced.

In some embodiment, the antihypertensive composition comprises acetate.

In some embodiments, the acetate comprises an $EC_{50}$ value in the antihypertensive composition in the range of from about 0.01 µM to about 0.3 µM.

In a preferred embodiment, the antihypertensive composition is sufficient to induce at least 50% activation of at least olfactory receptor OR51E1, olfactory receptor OR51E2, free fatty acid receptor FFAR2, free fatty acid receptor FFAR3 and/or hydroxycarboxylic acid receptor GPR109A in vivo when the antihypertensive composition is delivered to a patient.

In some embodiments, the antihypertensive composition comprises a delivery medium, propionic acid and 3-methylpentanoic acid, said propionic acid comprising an $EC_{50}$ value in the range of from about 0.05 µM to about 0.5 µM, said 3-methylpentanoic acid comprising an $EC_{50}$ value in the range of from about 5.0 µM to about 50.0 M, the antihypertensive composition similarly adapted to induce at least serotonin (5-HT), secretin, prostaglandin E2 and vasoactive intestinal protein secretion in vivo, whereby, when the antihypertensive composition is delivered to a patient, vasodilation is induced.

In some embodiment, the antihypertensive composition comprises butyrate.

In some embodiments, the butyrate comprises an $EC_{50}$ value in the antihypertensive composition in the range of from about 0.01 µM to about 0.3 µM.

In a preferred embodiment, the antihypertensive composition is sufficient to induce at least 50% activation of at least olfactory receptor OR51E1, olfactory receptor OR51E2, free fatty acid receptor FFAR2, free fatty acid receptor FFAR3 and/or hydroxycarboxylic acid receptor GPR109A in vivo when the antihypertensive composition is delivered to a patient.

In some embodiments of the invention, there are also provided methods for treating hypertension comprising the steps of:
  (a) providing an antihypertensive composition of the invention; and
  (b) delivering the antihypertensive composition to a patient presenting with hypertension, whereby vasodilation is induced.

As indicated above, the antihypertensive compositions can be delivered to a patient via any suitable means, including, without limitation, oral, sublingual, inhalation, intranasal, epidural, intracerebral, transdermal, topical, and injection means.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A composition for treating hypertension of a patient, comprising:
  propionic acid and butyrate, said propionic acid comprising an $EC_{50}$ value in the range of from about 0.05 µM to about 0.5 µM, said butyrate comprising an $EC_{50}$ value in the range of from about 0.01 µM to about 0.3 µM, said composition adapted to induce at least 50% activation of olfactory receptor family 51 subfamily E member 1 (OR51E1), olfactory receptor family 51 subfamily E member 2 (OR51E2), free fatty acid receptor 2 (FFAR2), free fatty acid receptor 3 (FFAR3) and hydroxycarboxylic acid receptor 2 (GPR109A) in vivo, whereby secretion of serotonin (5-HT), secretin, prostaglandin $E_2$ and vasoactive intestinal protein (VIP), and attenuated secretion of nuclear factor κ-B (NK-κB) and NADPH Oxidases (NOXs) are induced,
wherein said secretion of serotonin (5-HT), secretin, prostaglandin $E_2$ and VIP is sufficient to induce vasodilation of arterial vasculature of said patient, and said attenuated secretion of said NK—κB and NOXs is sufficient to abate renin secretion.

2. The composition of claim 1, wherein said $EC_{50}$ value of said propionic acid in said composition is in the range of from about 0.1 μM to about 0.2 μM.

3. The composition of claim 1, wherein said $EC_{50}$ value of said butyrate in said composition is in the range of from about 0.01 μM to about 0.02 μM.

4. The composition of claim 1, wherein said composition further comprises acetate.

5. The composition of claim 4, wherein said acetate comprises an $EC_{50}$ value in said composition in the range of from about 0.01 μM to about 0.3 μM.

* * * * *